(12) United States Patent
Grayson et al.

(10) Patent No.: US 12,357,188 B2
(45) Date of Patent: Jul. 15, 2025

(54) HIGH RESOLUTION TWO-DIMENSIONAL RESISTANCE TOMOGRAPHY

(71) Applicant: Northwestern University, Evanston, IL (US)

(72) Inventors: Matthew Allen Grayson, Evanston, IL (US); Chulin Wang, Evanston, IL (US); Claire Cecelia Onsager, Stoughton, WI (US); Can Cenap Aygen, Chicago, IL (US); Charles M. Costakis, Evanston, IL (US); Lauren E. Lang, Boulder, CO (US); Andreas Tzavelis, Demarest, NJ (US); John Ashley Rogers, Wilmette, IL (US)

(73) Assignee: Northwestern University, Evanston, IL (US)

( * ) Notice: Subject to any disclaimer, the term of this patent is extended or adjusted under 35 U.S.C. 154(b) by 911 days.

(21) Appl. No.: 17/295,318

(22) PCT Filed: Nov. 29, 2019

(86) PCT No.: PCT/US2019/063846
§ 371 (c)(1),
(2) Date: May 19, 2021

(87) PCT Pub. No.: WO2020/113157
PCT Pub. Date: Jun. 4, 2020

(65) Prior Publication Data
US 2022/0007958 A1    Jan. 13, 2022

Related U.S. Application Data

(60) Provisional application No. 62/772,369, filed on Nov. 28, 2018.

(51) Int. Cl.
*A61B 5/0536*    (2021.01)

(52) U.S. Cl.
CPC .................. *A61B 5/0536* (2013.01)

(58) Field of Classification Search
None
See application file for complete search history.

(56) References Cited

U.S. PATENT DOCUMENTS

| 6,940,286 B2 | 9/2005 | Wang et al. |
| 8,149,211 B2 * | 4/2012 | Hayakawa .......... G06F 3/04142 178/18.05 |

(Continued)

OTHER PUBLICATIONS

Lipponen, A., Seppänen, A., & Kaipio, J. (2013). Electrical impedance tomography imaging with reduced-order model based on proper orthogonal decomposition. Journal of Electronic Imaging, 22(2), 023008. doi.org/10.1117/1.jei.22.2.023008 (Year: 2013).*

(Continued)

*Primary Examiner* — May A Abouelela
*Assistant Examiner* — Samuel C Kim
(74) *Attorney, Agent, or Firm* — Benesch Friedlander Coplan & Aronoff LLP

(57) ABSTRACT

The disclosed 2-D and 3-D tomographic resistance imaging method improves tomographic resistance image resolution by adopting an orthogonal basis with the maximum number of elements N to describe the maximum resolution resistivity map $\rho(r)$, where this number of elements N is set according to the number of electrodes Q; by defining the orthogonal basis according to any known constraints in the problem, thereby enhancing the resolution where it is needed; by positioning electrodes to be sensitive to these basis functions; and by choosing current I and voltage V contact electrode pairs that maximize signal-to-noise ratio.

10 Claims, 6 Drawing Sheets

(56) References Cited

U.S. PATENT DOCUMENTS

| | | |
|---|---|---|
| 2009/0121727 A1 | 5/2009 | Lynch et al. |
| 2013/0044073 A1 | 2/2013 | Christiansson et al. |
| 2017/0241847 A1* | 8/2017 | Loh .......................... G01L 1/18 |
| 2018/0177430 A1 | 6/2018 | DeLimon et al. |

OTHER PUBLICATIONS

Kauppinen, Pasi, Jari Hyttinen, and Jaakko Malmivuo. "Sensitivity distribution visualizations of impedance tomography measurement strategies." International Journal of Bioelectromagnetism 8.1 (2006): 1-9. (Year: 2006).*

Player, M. A., et al. "An electrical impedance tomography algorithm with well-defined spectral properties." Measurement Science and Technology 10.3 (1999): L9. (Year: 1999).*

International Search Report and Written Opinion in International Application No. PCT/US19/63846, mailed Feb. 2, 2020 (8 pages).

Onsager, C., et al., "Sensitivity analysis for optimizing electrical impedance tomography protocols", arXiv preprint arXiv: 2111.01397. (Year: 2021).

\* cited by examiner (a) Symmetrically placed electrodes (sign error)

(b) Asymmetrically placed electrodes (correct sign)

(a) Neighboring I, V electrode pairs (lower signal-to-noise)

(b) Non-neighboring I, V electrode pairs (higher signal-to-noise)

HIGH RESOLUTION TWO-DIMENSIONAL RESISTANCE TOMOGRAPHY

CROSS-REFERENCE TO RELATED APPLICATIONS

The present application is a National Stage Entry of PCT International Patent Application No. PCT/US2019/063846 entitled "High Resolution Two-Dimensional Resistance Tomography," filed on Nov. 29, 2019, which claims priority to and the benefit of U.S. Provisional Patent Application Ser. No. 62/772,369 entitled "High Resolution Two-Dimensional Resistance Tomography," filed on Nov. 28, 2018, the disclosures of which are all hereby incorporated by reference in their entireties.

STATEMENT OF FEDERALLY FUNDED RESEARCH OR SPONSORSHIP

This invention was made with government support under grant numbers DMR1729016 and 1912694 awarded by the National Science Foundation. The government has certain rights in the inventions.

BACKGROUND OF THE DISCLOSURE

1. Technical Field

This disclosure relates to the field of two-dimensional (2-D) and three-dimensional (3-D) tomographic resistivity mapping and an improvement to mapping resolution.

2. Related Art

Two-dimensional resistance tomography utilizes a resistive elastomer sensing membrane to produce a change in resistance when contact pressure is applied. Resistance change is measured through periphery contact electrodes to generate a tomographic image of low resolution. To increase the tomographic image resolution, a large number of periphery contact electrodes are required to generate a large amount of data that is needed to feed computation intensive mesh algorithms. The amount of data and computational complexity does not assure that the measurements will converge to a solution, which wastes computing resources. In short, traditional algorithms suffer from wasted resources or suffer from low resolution that comes with failing to provide the required amount of data due to reliance on an ill-defined mesh problem in the algorithm, to poorly placed contact electrodes and to non-optimal electrode measurement pairs.

BRIEF DESCRIPTION OF DRAWINGS

The disclosure is better understood with reference to the following drawings and description. The elements in the figures are not necessarily to scale, emphasis instead being placed upon illustrating the principles of the disclosure. Moreover, in the figures, like-referenced numerals may designate to corresponding parts throughout the different views.

DETAILED DESCRIPTION

Figure 1A:
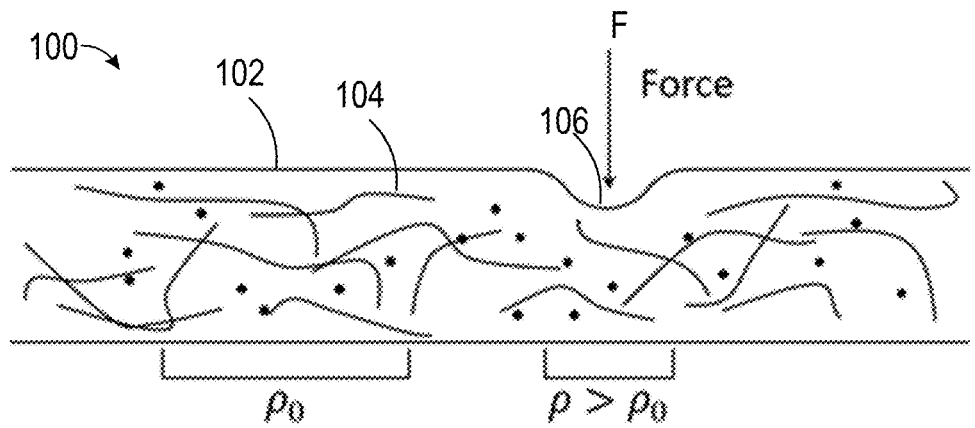
FIG. 1A is an exemplary resistive elastomer membrane and FIG. 1B is a pressure-sensitive demonstration of resistance change on the resistive elastomer membrane.
Figure 1B:
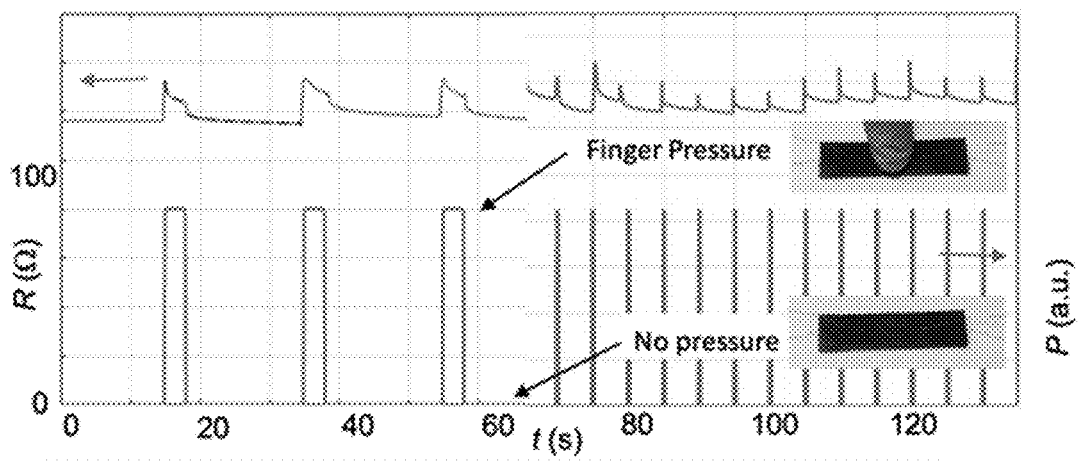

FIG. 1A is an exemplary resistive elastomer membrane 100 which is used in 2-D tomographic resistivity mapping. The resistive elastomer membrane 100 may be made of a composite of silicone elastomer 102 impregnated with pressure-sensitive carbon-nanotubes 104 having a resistivity of $\rho_0$. When a force F is applied to a surface area 106, the contact pressure causes a change in local resistivity, such as raising the local resistivity $\rho > \rho_0$ when the carbon-nanotubes 104 are compressed. FIG. 1B is a pressure-sensitive demonstration of resistance change on the resistive elastomer membrane.

Figure 2:
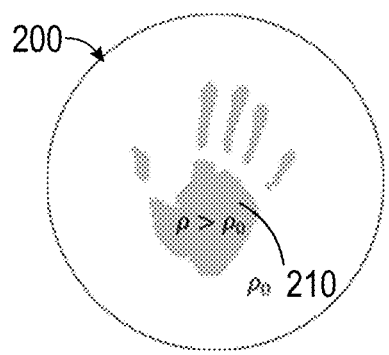
FIG. 2 is an exemplary tomographic resistivity map caused by resistivity change.

FIG. 2 is an exemplary tomographic resistivity map 210 on the resistive elastomer membrane 200 caused by a change in local resistivity $\rho > \rho_0$ due to contact pressure.

Figure 3A:
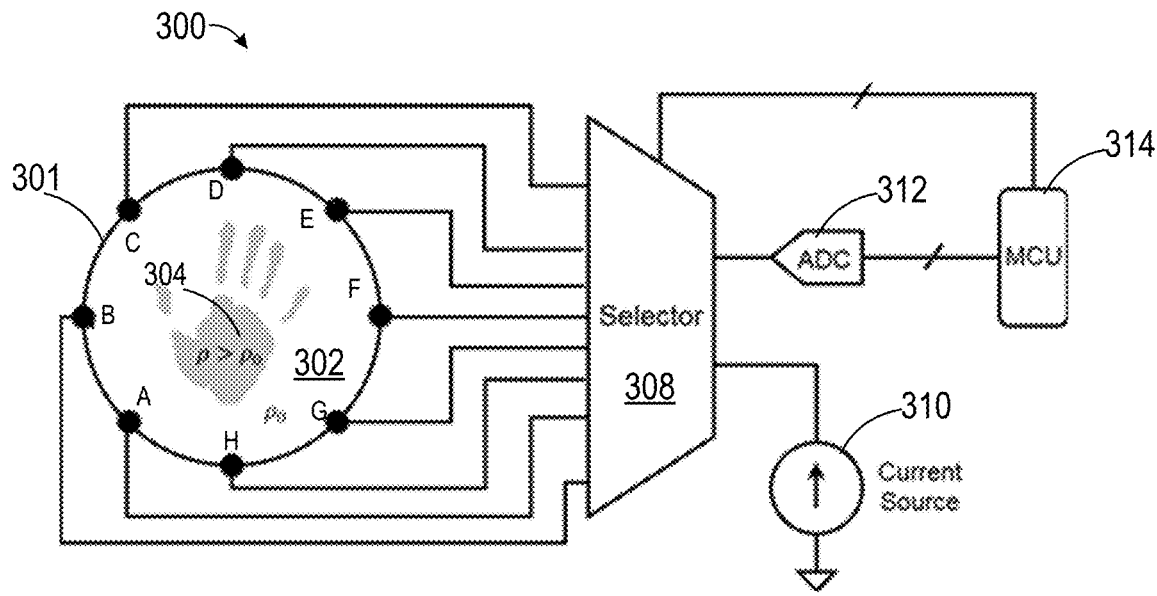
FIG. 3A illustrates an exemplary system to detect 2-D tomographic resistance image.

FIG. 3A illustrates an exemplary system 300 that detects a 2-D tomographic resistance image 304 on a resistivity map 302. In FIG. 3A, at least five electrode contacts (A to J) are attached along only periphery of the defined surface area 302 of the resistive sensing membrane 300. A resistance pattern caused by a contact pressure 304 is sensed by a combination of two contact electrode pairs (tetra-point) by simultaneously passing a current $I_{AB}$ 310 through a multiplexer 308 to the electrode pair AB rendering a voltage $V_{CD}$ at electrode pair CD.

The measured voltage $V_{CD}$ may be converted to digital format (e.g., digital data) through an analog to digital converter ADC 312. A respective tetra-polar resistance $(r_{ABCD})_i$ corresponding to a respective voltage and current ratio $(r_{ABCD})_i = V_{CD}/I_{AB}$ may be stored in a memory to be processed by a microcontroller MCU 314. Different electrode contact pairs such as EF and GH may also be simultaneously monitored as current leads and voltage probes until some or all N possible combination of electrode pairs are tested to measure the remaining tetra-polar resistances $(r_{ABCD})_i$ to $(r_{ABCD})_N$.

Accordingly, a 2-D tomographic image 304 over a surface 302 may be mapped by a computer implemented method by executing the following steps or operation. The first step defines a surface area 302 of a resistive sensing membrane 301 having Q periphery contact electrodes "A to H" that are attached along the periphery of the surface area of the resistive sensing membrane 301. In this step, Q is an integer (eight are illustrated in FIG. 3A) greater than or equal to five. A plurality of local area resistances $(r_{ABCD})_i$ to $(r_{ABCD})_N$ that vary with an applied contact pressure "F" over the defined surface area 302 of the resistive sensing membrane 301 causes a 2-D resistance variation.

The method further includes the step of mapping a 2-D resistance tomographic image 304 over the defined surface area 302 of the resistive sensing membrane 301. The mapping renders a plurality of local area resistance values $(r_{ABCD})_i$ to $(r_{ABCD})_N$ that reflect the applied contact pressure "F" to the surface area of the resistive sensing membrane.

The 2-D resistance tomographic image mapping further includes measuring the plurality of local area resistances $(r_{ABCD})_i$ to $(r_{ABCD})_N$ sequentially, over each and every N maximum combinations of two periphery contact electrode pairs from among the Q periphery contact electrodes "A to H". The result is a respective tetra-polar resistance $(r_{ABCD})_i$, wherein i=1 to N, and $$N = \frac{(Q-1)(Q-2)}{2},$$

wherein each respective tetra-polar resistance $(r_{ABCD})_i$ corresponds to a respective voltage and current ratio $(r_{ABCD})_i = V_{CD}/I_{AB}$, such that a respective voltage $V_{CD}$ is established across a first periphery contact electrode pair CD when a respective current $I_{AB}$ is simultaneously passed across a second periphery contact electrode pair AB. The first periphery contact electrode pair CD is different from the second periphery contact electrode pair AB, wherein the respective tetra-polar resistance $(r_{ABCD})_i$ reflects a local area resistance variation in a resistivity map $\rho(r)$ of the 2-D resistance tomographic image. The resistivity map $\rho(r)$ is related to the orthogonal basis polynomial functions $\phi_i(r)$ by $\rho(r) = \Sigma_i a_i \phi_i(r)$, and the resistivity map $\rho(r)$ is formed by superimposing the orthogonal basis polynomial functions $\phi_i(r)$. The orthogonal basis polynomial functions $\phi_i(r)$ have a resolution that increases with a degree of freedom set at an upper limit that is the same as the maximum combinations of N measurements. Here "a" is comprised of "a1, a2, . . . ai, . . . " that represent ordered vector coefficients. The 2-D resistance tomographic image is displayed through the resistivity map $\rho(r)$ on the defined surface 302.

Figure 3B:
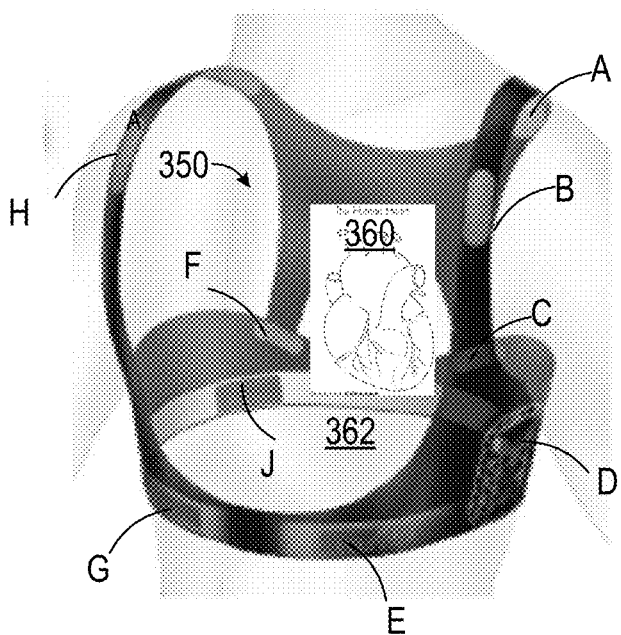
FIG. 3B illustrates an alternate detecting of a 3-D tomographic resistance image through volume resistance measurement.

FIG. 3B is an alternate detection of a 3-D tomographic resistance image 360 through a volume resistance measurement. In FIG. 3B, a 3-D tomographic resistance image 360 (such as an image of a human heart) may be sensed and detected through volume resistance measurements using a similar mapping algorithm and by a direct electrode placement over a defined volume boundary such as a human torso 350, for example, the human skin is a resistive membrane which encloses a resistive volume such as a human torso 350.

The computer implemented algorithm is modified to map a tomographic image 360 across a volume 350 beneath a surface 362. The method includes defining a resistive volume 350 having Q surface contact electrodes A to J attached on the defined surface area 362 of the resistive volume 350. Q is an integer, such as nine in this example (e.g., preferably greater than or equal to five), where a plurality of local volume resistances $(r_{ABCD})_i$ to $(r_{ABCD})_N$ are defined. The local volume resistances vary with depth and material compositions (e.g., the tissue types and densities) beneath the defined surface area 362 of the resistive volume 350. The variations cause a three-dimensional (3-D) resistance variation. The method further includes mapping a 3-D resistance tomographic image over the defined resistive volume 350 according to the plurality of local volume resistances $(r_{ABCD})_i$ to $(r_{ABCD})_N$ beneath the defined surface area 362 of the resistive volume 350.

The 3-D resistance tomographic image mapping further includes measuring the plurality of local volume resistances $(r_{ABCD})_i$ to $(r_{ABCD})_N$ sequentially, over each and every N maximum combinations of two periphery contact electrode pairs (e.g., AB, CD, etc.) from among the Q periphery contact electrodes A to J. The result is a respective tetra-polar resistance $(r_{ABCD})_I$ measure where i=1 to N, and $$N = \frac{(Q-1)(Q-2)}{2}.$$

Each of the respective tetra-polar resistance $(r_{ABCD})_i$ corresponds to a respective voltage and current ratio $(r_{ABCD})_i = V_{CD}/I_{AB}$. A respective voltage $V_{CD}$ is established across a first surface contact electrode pair CD when a respective current $I_{AB}$ is simultaneously passed between a second surface contact electrode pair AB. The first surface contact electrode pair CD is different from the second surface contact electrode pair AB. The respective tetra-polar resistance $(r_{ABCD})_i$ reflects a local volume resistance variation in a resistivity map $\rho(r)$ of the 3-D resistance tomographic image. The resistivity map $\rho(r)$ is related to orthogonal basis polynomial functions $\phi_i(r)$ that is part of the expression $\rho(r) = \Sigma_i a_i \phi_i(r)$. The resistivity map $\rho(r)$ is formed by superimposing the orthogonal basis polynomial functions $\phi_i(r)$. The map has a resolution that increases with a degree of freedom set at an upper limit same as the maximum combinations of N. The variable "a" is comprised of "$a_1$, $a_2$, . . . $a_i$, . . . ", which are the ordered vector of coefficients. The detection displays the 3-D resistance tomographic image through the resistivity map $\rho(r)$ beneath the defined area 362.

The disclosed method improves tomographic resistance image resolution by adopting an orthogonal basis with a maximum number of elements N, which renders a maximum resolution resistivity map $\rho(r)$. The number of elements N is determined by the number of electrodes Q. The detection defines the orthogonal basis according to any known constraints in a problem, thereby enhancing the resolution where ever it is needed. The detection positions the electrodes such that they are sensitive to these basis functions. The selection of current I and voltage V contact electrode pairs maximize the signal-to-noise ratio output.

Some standard methods for electrical impedance tomography solve the inverse mapping problem by defining thousands of mesh points to represent a resistance map that is consistent with a much smaller set of measurements that is orders of magnitude smaller in size than the disclosed detection. As such, these finite-element methods present an ill-defined problem such that the number of variables to be solved greatly exceeds the number of equations required to constrain them. Under these conditions, a large amount of computational power is wasted on calculating an unnecessarily large number of mesh points, and the resulting solution is not unique, depending on the choice of mesh or other minor boundary conditions. Subsequently, a regularization procedure must be performed to include a cost-function in the solution to artificially induce smoothness in the final result.

More specifically, the disclosed 2-D and 3-D methods devise an alternate strategy for the inverse problem in electrical impedance tomography, which improves detection resolutions and reduces computational time. The 2-D and 3-D methods takes the following approaches:

(1) Set the number of orthogonal basis functions for the resistivity map N equal to the maximum number of independent resistance measurements, thereby guaranteeing a maximum resolution. If Q is the number of contacts, then the number of independent measurements N is:

$$N = \frac{(Q-1)(Q-2)}{2} \quad (1)$$

The number basis functions may be restricted to the number of degrees of freedom, which make the solution unique, rather than ill-defined.

(2) Execute a set of orthogonal basis functions $\phi_i(r)$ to describe the resistivity map $\rho(r)$. Traditional tomographic methods may define a high-resolution mesh with thousands of points to describe the resistivity map. The mesh points are not independent of each other, as such they must be artificially correlated by adding an additional cost-function term in a regularization procedure. However, the disclosed approach executes an orthogonal basis functions $\phi_i(r)$ to describe the resistivity map $\rho(r)$. The resistivity map $\rho(r)$ may be described as an ordered vector of coefficients $a=(a_1, a_2, \ldots a_i, \ldots)$ that may be expressed by equation 2.

$$\rho(r)=\Sigma_i a_i \phi_i(r) \quad (2)$$

Such basis functions may be proposed a priori from a set of orthogonal polynomials, or may be derived from a covariant analysis of a set of known resistivity maps.

Figure 4:
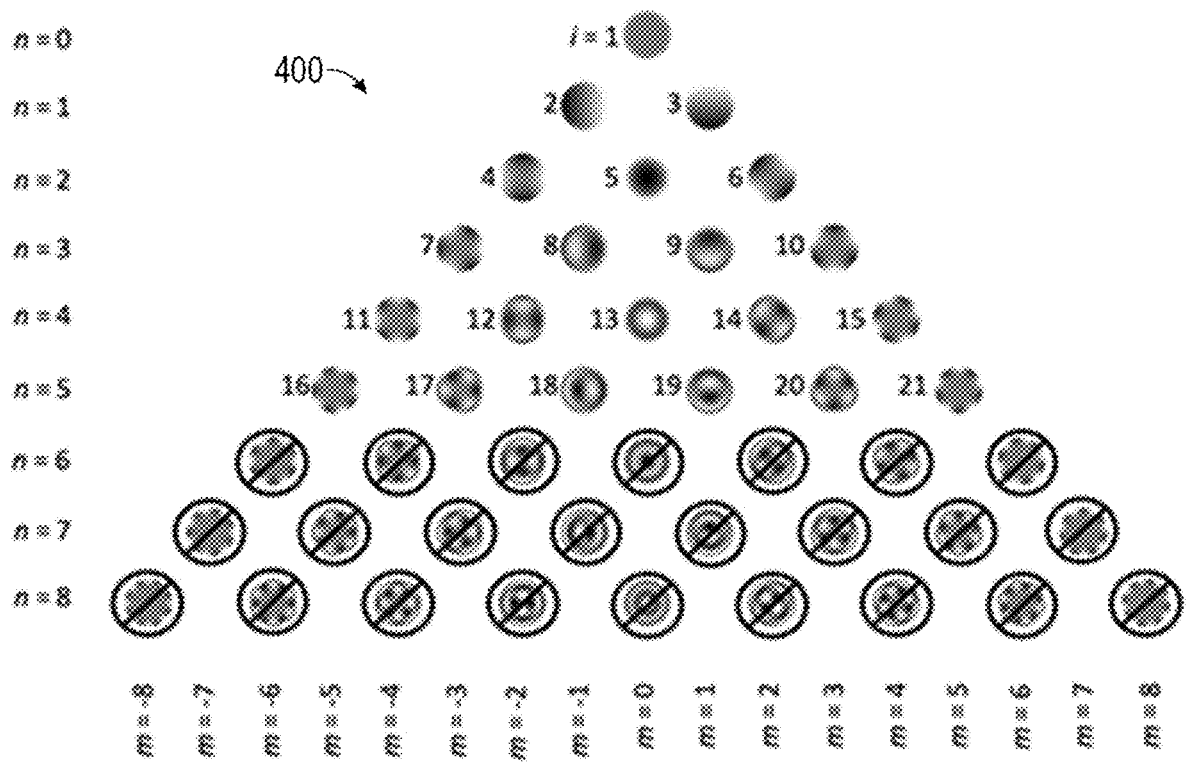
FIG. 4 illustrates an exemplary set of orthogonal polynomial functions defined by a circular surface.

For 2-D tomographic resistance imaging, the defined surface area 302 of the resistive sensing membrane 301 may comprise any arbitrary shape. For simplification, in a use case where the defined surface area 302 is circular, the orthogonal basis polynomial functions $\phi_i(r)$ may be a priori polynomial basis functions described by the Zernike polynomial equations, as shown in FIG. 4. FIG. 4 illustrates an exemplary set of orthogonal polynomial functions defined by a circular surface as expressed below.

$$Z_n^m(\rho, \varphi) = \begin{cases} R_n^m(\rho)\cos(m\varphi); & \text{for } m \text{ even} \\ R_n^m(\rho)\sin(m\varphi); & \text{for } m \text{ odd} \end{cases} \quad (3)$$

$$R_n^m(\rho) = \begin{cases} \sum_{k=0}^{\frac{n-m}{2}} \frac{(-1)^k(n-k)!}{k!\left(\frac{n+m}{2}-k\right)!\left(\frac{n-m}{2}-k\right)!}\rho^{n-2k}; & \text{for } n-m \text{ even} \\ 0; & \text{for } n-m \text{ odd} \end{cases}$$

The integer $n=\{0, 1, 2, \ldots\}$ ranks the resolution of the polynomial from low to high, and m satisfies $-n \leq m \leq n$. The radial function is described by $R_n^m(\rho)$ and the azimuthal function is a sine or cosine function with a harmonic order m. These basis functions are all orthogonal to each other, the coefficient vector "a" in Eq. 2 represents a compact expression of the complete set of all possible resistivity maps described by the basis, where a cutoff assuming the maximum number of allowable basis states N is imposed, where in FIG. 4, N=21.

For 3-D tomographic resistance imaging, the volume may have an arbitrary shape. For simplification in a use case when the defined volume is spherical, the orthogonal basis polynomial functions $\phi_i(r)$ are a priori polynomial basis functions may be described by spherical harmonic equations: expressed below.

$$S_l^m(\rho,\theta,\varphi)=\rho^l Y_l^m(\theta,\varphi)$$

$$Y_l^m(\theta,\varphi)=e^{im\varphi} P_l^m(\cos\theta)$$

where the functions $P_l^m(x)$ are associated Legendre polynomials:

$$P_l^m(x) = (-1)^m 2^l (1-x^2)^{m/2} \sum_{k=m}^{l} \frac{k!}{(k-m)!} x^{k-m} \binom{l}{k} \binom{\frac{l+k-1}{2}}{l}$$

such that the integer $l=\{0, 1, 2, \ldots\}$ ranks the resolution of the polynomial from low to high, and m satisfies $-l \leq m \leq +l$.

Figure 5:
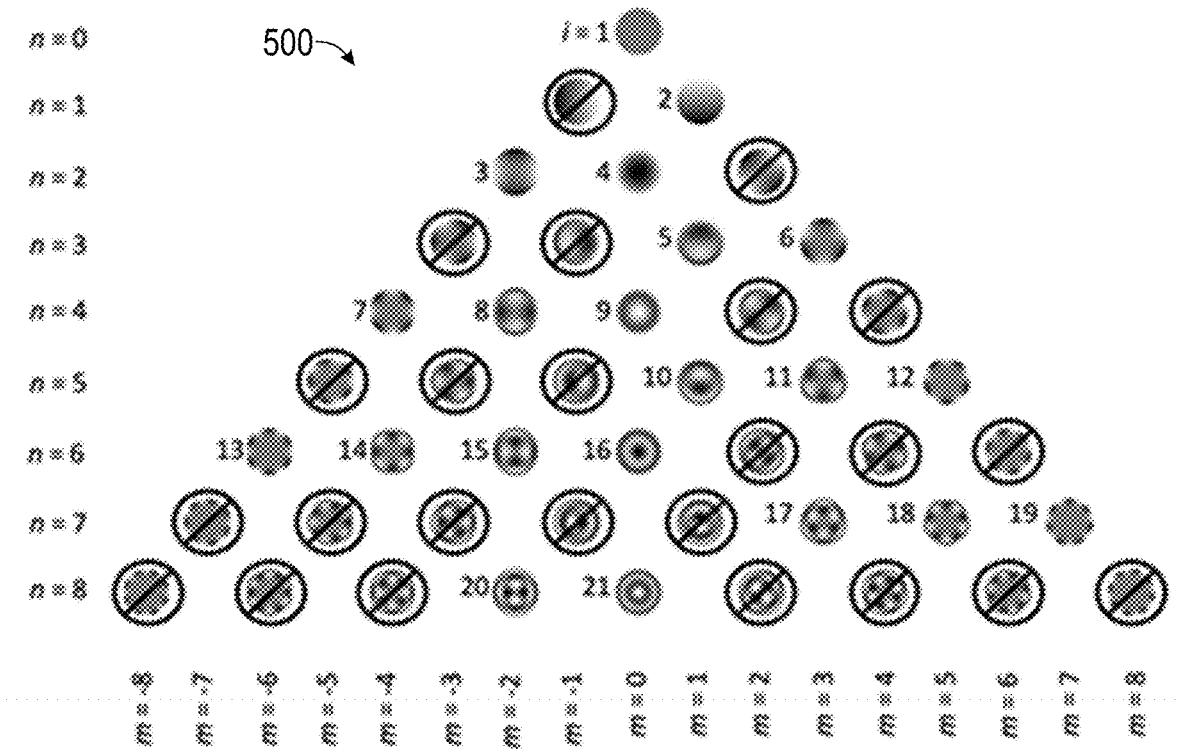
FIG. 5 illustrates a modified set of orthogonal polynomial functions to enhance image resolution under an unknown constraint.

A second example of an a priori polynomial basis may be a constrained polynomial basis. FIG. 5 illustrates a modified set of orthogonal polynomial functions that enhance image resolution under a constraint. FIG. 5 shows a case that the resistivity map is known to be mirror-symmetric in the x-coordinate plane. A subset of these basis states can then be disallowed (e.g., constrained), and are crossed off, accordingly, in the figure. The remainder of the allowable basis states are indexed "i" from a low to a high resolution, accordingly to control resolution at a maximum limit with a value of N=21.

A third example of an orthogonal basis is determined by applying a principle component analysis (PCA) to a representative set of likely resistance maps "a". The covariance matrix of the resistance maps may be expressed as:

$$\text{Cov}(a)=\Gamma_a$$

which can be diagonalized $$\Gamma_a = W^T \Lambda W$$

where the matrix $\Lambda$ is a diagonal matrix, and $WW^T=I$.

$$\Lambda = \text{diag}(\lambda_1, \lambda_2, \ldots, \lambda_N)$$

The eigenvalues of the covariance matrix can be ordered $\lambda_1 \geq \lambda_2 \geq \ldots \geq \lambda_N$, and the largest $\hat{N}$ eigenvalues of the covariance matrix as the principle components.

$$\Gamma_a^{PCA} = W^T \Lambda^{PCA} W, \Lambda^{PCA} = \text{diag}(\lambda_1, \lambda_2, \ldots, \lambda_{\hat{N}}, 0, \ldots, 0)$$

Here W is comprised of all eigenvectors, $W=[w_1\ w_2\ \ldots\ w_N]$. Thus, the orthogonal basis then can be represented by the reduced basis $w_1, w_2, \ldots w_{\hat{N}}$, and the eigenvectors W of the covariance matrix with largest eigenvalues $\square$N are used as orthogonal basis functions with index i whose upper limit N is the same as the maximum number of independent tetrapolar measurements.

A fourth example of an orthogonal basis is a combination of the above methods (e.g., a priori, constrained, and principle component analysis basis functions). In this example, the principle component analysis of the third method may reveal only a limited number $\hat{N}$ of basis functions before the covariance vanishes into the noise. But since the total number of independent measurements in the problem is N from Eq. 1, the disclosed method allows the remaining $N-\hat{N}$ basis functions to be determined as a priori polynomial functions or constrained a priori polynomial functions, chosen to be orthogonal to the N members of the principle component basis.

Another approach tailors the choice of orthogonal basis functions to the highest resolution in the constrained region where the information is most critical relative to a known background or other constraint. This approach overcomes the disadvantages in uniform finite element meshes over a volume. If the region of interest in finite element meshes is local within that volume, then computational time and mathematical resolution is wasted on regions that are not useful.

If there are constraints and/or local regions of interest in the tomographic problem, then the orthogonal basis functions can be restricted to map features within only that region. Thus, the full power of the tomographic resolution is devoted to the region where information is needed.

The disclosed detections select electrode locations that have the highest resolution in discerning the orthogonal basis functions of interest. Current tomographic methods may place contacts at regular intervals around the periphery of the resistive object's volume to be mapped. This is detrimental for two reasons.

Figure 8:
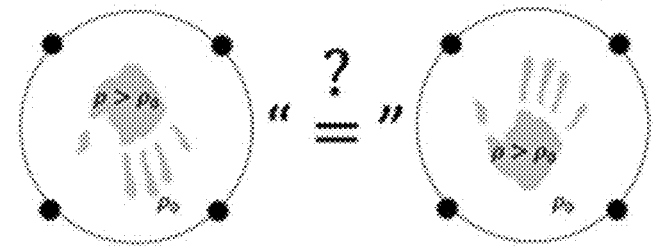
FIG. 8 illustrates the importance of having asymmetrically placed contact electrodes to eliminate sign errors in the mapping algorithm.
Figure 8:
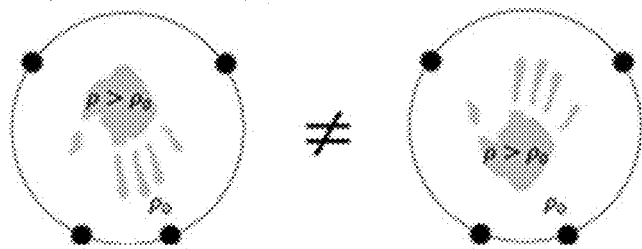

First, symmetric placement of contacts may result in a reduced number of independent measurements, reducing the maximum achievable resolution of the resistivity map. This point is illustrated in FIG. 8 where symmetric placement of four contact electrodes would yield the same tetra-polar resistance values for the correct tomographic image as for its inverted image, whereas asymmetrically placed contact electrodes would yield different tetra-polar resistances for the original image and its inverse.

Second, many tomographic systems may have a known background resistivity. The goal is to map only deviations from the resistivity. Strategic placement of contact electrodes may result in maximum sensitivity to these deviations. The disclosed detection applies the orthogonal basis functions to determine where contact electrodes should be placed to have maximum sensitivity in discerning independent measurements.

Figure 9:
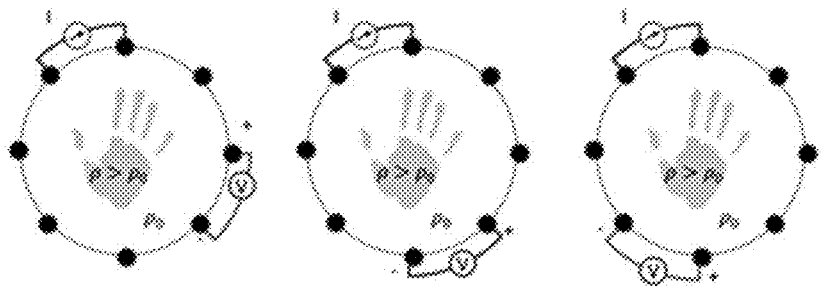
FIG. 9 illustrates electrode configurations for improving the signal-to-noise ratio.
Figure 9:
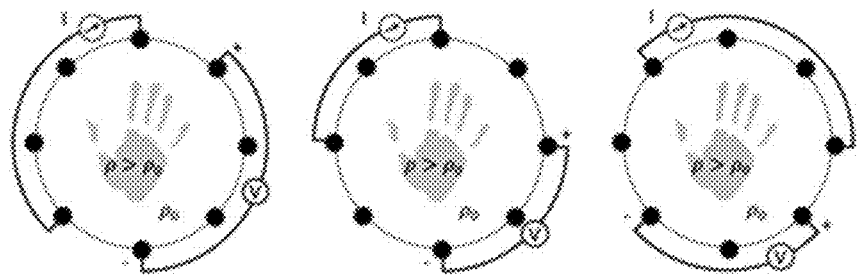

The detections also identify what pairs of current and voltage electrodes should be measured to provide the maximally independent set of complete measurements while maximizing signal-to-noise measurements. There are very many ways to collect a complete measurement set of N independent tetra-polar resistances, and by optimizing the choice of current-electrode pairs and voltage-electrode pairs, the disclosed detection makes it possible to choose a set that gives maximally independent measurements, and a maximal signal-to-noise ratio output. This is illustrated in FIG. 9 where the standard method (top row) is shown to use neighboring contact pairs for +/−current I and +/−voltage V, which leads to small voltage signals when the voltage pair is on the opposite side of the sample from the current pair. However, a tetra-polar resistance that has a larger distance between the + and − leads for both current I and voltage V (bottom row) will have larger voltage signals, and therefore lead to higher accuracy tomographic mapping. This maximally independent and maximal signal-to-noise output set of complete measurements can be predetermined through simulations.

An exemplary application of a tomographic device is a pressure-sensitive polymer pad infused with carbon-nano-tubes, carbon-black, or a combination of conductive particles that cause the polymer resistivity to change locally under an applied force as shown in FIG. 1. An exemplary tomographic sensor comprises a circular area of a pressure-sensitive polymer, with a pressure pattern, such as a handprint, causing local resistivity changes $\rho(r)$ as shown in FIG. 2. In FIG. 2 the bottom trace of the graph shows the applied pressure d either in a square wave (left) or in spikes (right), and the top trace of the graph shows a clear resistivity response, accordingly.

The resistivity pattern can be measured as shown in FIG. 3 with a series of resistivity measurements through electrodes at the periphery of the sensor. A microcontroller unit (MCU) can regulate a selector to cycle through different electrode pairs used as current and voltage electrodes. When the current between two electrodes is applied, the voltage across two different electrodes is measured. Each resulting measurement is fed into an analog-to-digital converter and then back to the MCU which will store this measurement in memory and then direct the next measurement to be started. The complete set of independent measurements with N different elements is called the measurement vector $M_{measured}$.

In FIG. 5, the central computer reads the measurement vector $M_{measured}$ from the memory of the MCU and conducts an iterative loop to determine what the resistivity map must be to generate this measurement vector. A candidate resistivity map of the sample $\rho_{predicted}(r)$ is chosen and its resulting measurement vector $M_{predicted}$ is derived. If the two measurement vectors are different, then the predicted sample resistivity is adjusted using a quasi-Newton method, simulated annealing, or a similar self-consistent recursive method, and the process iterated until the two measurement vectors are identical within a specified tolerance.

In FIG. 3, an example of a basis functions for a circular sample are shown, where it is assumed that twenty-one (N=21) unique measurements can be performed, therefore the basis will consist of twenty-one different polynomial functions that are mutually orthogonal over the sample area. In this use case, a common orthogonal set of basis functions comprise the Zernike polynomials, exhibited graphically in FIG. 3. Only the first twenty-one basis functions are used, hence the remaining crossed out polynomials indicates functions whose resolution is higher than what can be achieved with 21 different measurements. The solid black line indicates functions whose resolution is higher than what can be achieved with the twenty-one different measurements. The resistivity is expressed in terms of these basis functions according to Eq. 1 above.

The detection identifies which pairs of current and voltage electrodes are measured to provide maximal independence. In FIG. 4, an example of a constrained basis is shown. In this use case, the resistivity map is symmetric in the x-plane and the twenty-one basis functions need not include functions that violate this symmetry. Overall, the resolution can be enhanced to finer details as seen in the size of the features at the bottom row of FIG. 4.

Figure 6:
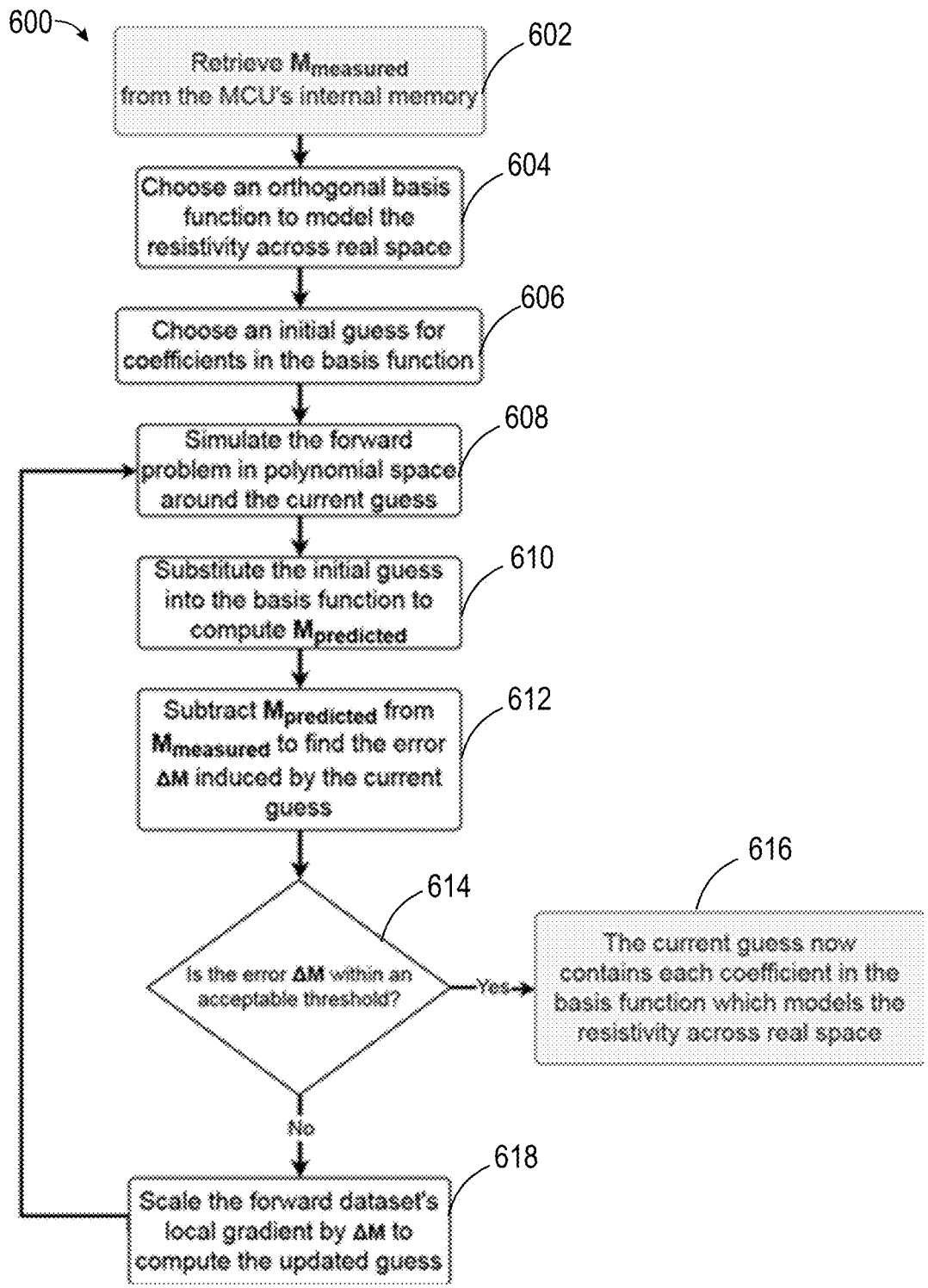
FIG. 6 illustrates an exemplary algorithm to carry out tomographic mapping.

FIG. 6 illustrates an exemplary algorithm that executes the tomographic mapping. Flow chart of the algorithm invert the resistance measurements to derive the local resistance pattern. In step 602, the resistance measurement vector $M_{measured}$ may be retrieved from the MCU. In step 604, the detection selects an orthogonal basis function to model the resistivity across real space. In step 606, the detection establishes the coefficients based on an empirical estimate in the basis function. In step 608, the detection simulates a forward problem in polynomial space around the current estimate. In step 610, the detection substitutes the initial estimate into the basis function to compute $M_{predicted}$. In step 612, the detection subtracts $M_{predicted}$ from $M_{measured}$ to derive the error $\Delta M$ induced by the current estimate. The result is compared to the resistance measurement vector $M_{predicted}$ derived from the initial estimate at the coefficients for the resistivity map basis functions. The two measurement vectors are compared in step 614. If the error ΔM falls within a predetermined threshold, the current estimate will contain each coefficient in the basis function which models the resistivity across real space. If it does not fall within the predetermined threshold, the process scale the forward database's local gradient by ΔM to compute the updated estimate, and the estimate is iteratively updated until the two become equal within the specified tolerance and the process repeats at step 608.

Figure 7:
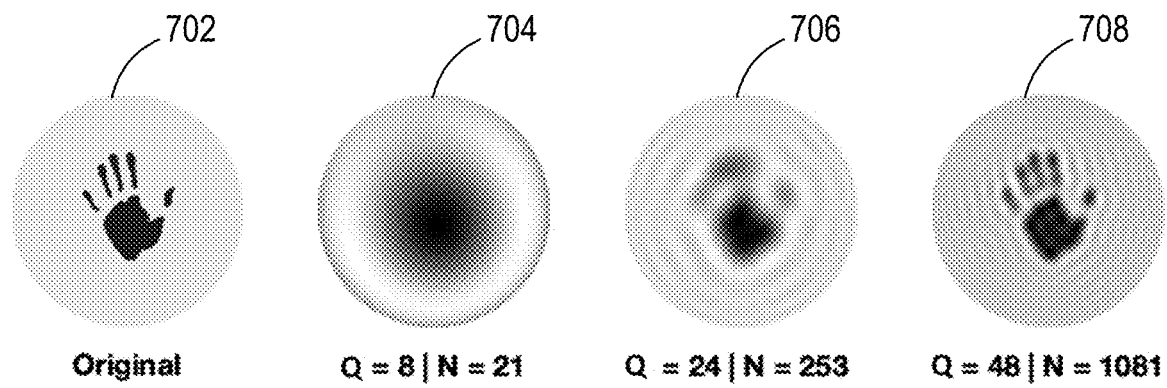
FIG. 7 illustrates different resolutions of tomographic resistance image with increasing number of contact electrodes.

FIG. 7 illustrates different resolutions of tomographic resistance image. An original 2D map example of a handprint (left) may be measured with maximum achievable resolution for Q=8 contact electrodes (N=21 independent measurements), Q=24 contact electrodes (N=253 independent measurements), and Q=48 contact electrodes (N=1081 independent measurements). The maximum resolution of the image clearly depends on the number of contacts and possible tetra-polar resistance measurement combinations.

FIG. 8 illustrates how placement of contact electrodes can affect the accuracy of the measurement. If, for example, the tomographic area is top-to-bottom reflection symmetric (in this case the shape of a circle) and the contact electrode placement is also top-to-bottom reflection symmetric (top row), then all tetra-polar resistances measured using these contacts cannot distinguish between the correct hand image and its top-to-bottom reflected mirror image. However, if the contact electrodes are placed asymmetrically (bottom row) so as to not possess top-to-bottom reflection symmetry, the contact electrodes would measure different tetra-polar resistances for the correct hand image and its top-to-bottom reflected mirror image, thereby gathering more information about the sample of interest via asymmetric placement of contact electrodes.

FIG. 9 illustrates how choice of contact electrode pairs can increase the signal and therefore increase the accuracy and resolution of the measurement. The top row illustrates the standard method of choosing tetra-polar resistances whereby neighboring contact electrodes are used as voltage and current electrode pairs to constitute a complete set of N independent tetra-polar measurements. However when the neighboring pairs are on opposite sides of the sample, the signal voltage can be quite small, reducing the signal-to-noise ratio. On the other hand, the measurements on the bottom row will have larger signals since the positive current electrode is closer to the positive voltage electrode, and the negative current electrode is closer to the negative voltage electrode. The complete set of N independent tetra-polar measurements will therefore have a larger signal-to-noise ratio and demonstrate increased accuracy.

The functions, acts or tasks illustrated in the FIGS. or described may be executed in a digital and/or analog domain and in response to one or more sets of logic or instructions stored in or on non-transitory computer readable medium or media or memory. The functions, acts or tasks are independent of the particular type of instructions set, storage media, processor or processing strategy and may be performed by software, hardware, integrated circuits, firmware, microcode and the like, operating alone or in combination. The memory may comprise a single device or multiple devices that may be disposed on one or more dedicated memory devices or disposed on a processor or other similar device. When functions, steps, etc. are said to be "responsive to" or occur "in response to" another function or step, etc., the functions or steps necessarily occur as a result of another function or step, etc. It is not sufficient that a function or act merely follow or occur subsequent to another. The term "substantially" or "about" encompasses a range that is largely (anywhere a range within or a discrete number within a range of ninety-five percent and one-hundred and five percent), but not necessarily wholly, that which is specified. It encompasses all but an insignificant amount.

Other systems, methods, features and advantages will be, or will become, apparent to one with skill in the art upon examination of the figures and detailed description. It is intended that all such additional systems, methods, features and advantages be included within this description, be within the scope of the disclosure, and be protected by the following claims.

We claim:

1. A computer implemented method for mapping a tomographic image over a surface, comprising:

defining a surface area of a resistive sensing membrane having Q periphery contact electrodes attached along a periphery of the defined surface area of the resistive sensing membrane, wherein Q comprises an integer higher than or equal to five, wherein the resistive sensing membrane comprises a plurality of local area resistances $(r_{ABCD})_i$ to $(r_{ABCD})_N$, wherein the plurality of local area resistances $(r_{ABCD})_i$ to $(r_{ABCD})_N$ vary when an applied contact pressure is applied over the defined surface area of the resistive sensing membrane, wherein the applied contact pressure causes a two-dimensional (2-D) resistance variation;

mapping a 2-D resistance tomographic image over the defined surface area of the resistive sensing membrane according to the plurality of local area resistances of the applied contact pressure to the defined surface area of the resistive sensing membrane, wherein the 2-D resistance tomographic image mapping comprises:

measuring a respective tetra-polar resistance of the plurality of local area resistances $(r_{ABCD})_i$ to $(r_{ABCD})_N$ sequentially, wherein i=1 to N, and N represents a maximum number of independent tetra-polar measurements, wherein each respective tetra-polar resistance corresponds to a respective voltage and current ratio $r_{(ABCD)i}=V_{CD}/I_{AB}$, such that a respective voltage $V_{CD}$ is established across a first periphery contact electrode pair CD when a respective current $I_{AB}$ is simultaneously passed across a second periphery contact electrode pair AB, wherein the first periphery contact electrode pair CD is different from the second periphery contact electrode pair AB, wherein the respective tetra-polar resistance reflects a local area resistance variation in a resistivity map ρ(r) of the 2-D resistance tomographic image;

wherein the resistivity map ρ(r) is related to orthogonal basis polynomial functions $\phi_i(r)$ by an equation of $\rho(r)=\Sigma_i a_i \phi_i(r)$, and the resistivity map ρ(r) is formed by superimposing the orthogonal basis polynomial functions $\phi_i(r)$ having a resolution that increases with index i whose upper limit N is the same as a maximum number of independent tetra-polar resistance measurements, wherein $a=(a_1, a_2, \ldots a_i, \ldots)$ are ordered vector of coefficients; and displaying the 2-D resistance tomographic image through the resistivity map ρ(r) on the defined surface.

2. The computer implemented method according to claim 1, wherein the defined surface area of the resistive sensing membrane is an arbitrary shape, and in a case when the defined surface area is circular, the orthogonal basis polynomial functions $\phi_i(r)$ are a priori polynomial basis functions described by the Zernike polynomial equations:

$$Z_n^m(\rho, \varphi) = \begin{cases} R_n^m(\rho)\cos(m\varphi); & \text{for } m \text{ even} \\ R_n^m(\rho)\sin(m\varphi); & \text{for } m \text{ odd} \end{cases}$$

$$R_n^m(\rho) = \begin{cases} \sum_{k=0}^{\frac{n-m}{2}} \frac{(-1)^k(n-k)!}{k!\left(\frac{n+m}{2}-k\right)!\left(\frac{n-m}{2}-k\right)!}\rho^{n-2k}; & \text{for } n-m \text{ even} \\ 0; & \text{for } n-m \text{ odd} \end{cases}$$

whereby the integer n={0, 1, 2, ... } ranks the resolution of the polynomial from low to high, and m satisfies $-n \leq m \leq n$.

3. The computer implemented method according to claim 2, wherein the orthogonal basis polynomial functions $\phi_i(r)$ is a constrained polynomial basis having a subset of basis states being disallowed, wherein a remainder of allowable basis states are indexed from low to high resolutions.

4. The computer implemented method according to claim 3, wherein the orthogonal basis functions $\phi_i(r)$ are determined by applying a principle component analysis (PCA) to a representative set of likely resistance maps a, as a way to generate basis functions which are sensitive to the most important variations in a resistivity profile, wherein the covariance matrix of the resistance map is calculated from equation:

$$\text{Cov}(a) = \Gamma_a$$

which can be diagonalized $$\Gamma_a = W^T \Lambda W$$

where the matrix $\Lambda$ is a diagonal matrix, and $WW^T = I$, $$\Lambda = \text{diag}(\lambda_1, \lambda_2, \ldots, \lambda_N)$$

wherein the eigenvalues $W=[w_1, w_2, \ldots, w_N]$ of the covariance matrix can be ordered $\lambda_1 \geq \lambda_2 \geq \ldots \geq \lambda_N$, and the largest $\hat{N}$ eigenvalues of the covariance matrix as the principle components for principle component analysis (PCA), where $$\Gamma_a^{PCA} = W^T \Lambda^{PCA} W, \Lambda^{PCA} = \text{diag}(\lambda_1, \lambda_2, \ldots, \lambda_{\hat{N}}, 0, \ldots, 0)$$

Here W is comprised of all eigenvectors, $W=[w_1, w_2, \ldots, w_N]$, Thus, the orthogonal basis then can be represented by the reduced basis $w_1, w_2, \ldots w_{\hat{N}}$, and the eigenvectors W of the covariance matrix with largest eigenvalues $\lambda_{\hat{N}}$ are used as orthogonal basis functions with index i whose upper limit N is the same as the maximum number of independent tetra-polar measurements.

5. The computer implemented method according to claim 4, wherein the orthogonal basis functions $\phi_i(r)$ are determined by a combination of the a priori polynomial basis, the constrained polynomial basis, and the PCA basis functions having a resolution that increases with index i whose upper limit N is the same as the maximum number of independent tetra-polar measurements.

6. The computer implemented method according to claim 5, wherein a choice of the orthogonal basis functions $\phi_i(r)$ having are chosen from a highest resolution in a constrained region is within the constrained.

7. The computer implemented method according to claim 5, wherein in presence of the constraints, the method further comprising restricting, when constraints are present, the orthogonal basis functions $\phi_i(r)$ to map features within only local regions of interest.

8. The computer implemented method according to claim 1, further comprising choosing locations of the periphery contact electrodes to have highest resolution to discern the orthogonal basis functions $\phi_i(r)$.

9. The computer implemented method according to claim 1, further comprising identifying what pairs of current and voltage electrodes should be measured to provide a maximally independent set of complete measurements while maximizing signals.

10. The computer implemented method according to claim 1, wherein a measured resistance vector is calculated from the respective tetra-polar resistances that were measured.

* * * * *